United States Patent [19]
Griffin

[11] Patent Number: 5,388,269
[45] Date of Patent: Feb. 14, 1995

[54] EYE SHIELDING APPARATUS AND METHOD

[75] Inventor: Bradley P. Griffin, Greenville, N.C.
[73] Assignee: Practicon, Inc., Greenville, N.C.
[21] Appl. No.: 118,024
[22] Filed: Sep. 8, 1993
[51] Int. Cl.⁶ ............................................. A61F 9/04
[52] U.S. Cl. ................................... 2/13; 2/449; 351/47; 351/123
[58] Field of Search ............... 2/13, 449, 450, 431, 2/448; 351/47, 123

[56] References Cited

U.S. PATENT DOCUMENTS

| | | |
|---|---|---|
| 971,372 | 9/1910 | Hamilton ................................ 2/13 |
| 2,093,536 | 9/1937 | Alvord .................................. 2/13 |
| 2,253,101 | 8/1941 | Thoreson ............................... 2/13 |
| 2,281,129 | 4/1942 | Wolff .................................... 2/13 |
| 2,541,242 | 2/1951 | Grove ................................... 2/13 |
| 2,823,385 | 2/1958 | Watkins . | |
| 2,932,066 | 4/1960 | Lindblom . | |
| 3,436,761 | 4/1969 | Liautaud et al. . | |
| 3,505,679 | 4/1970 | Bennett . | |
| 3,932,031 | 1/1976 | Johnston . | |
| 4,726,075 | 2/1988 | Hinrichs . | |
| 4,751,746 | 6/1988 | Rustin ............................... 351/123 X |

FOREIGN PATENT DOCUMENTS 0609004 11/1960 Canada .................................. 351/47
0652728 11/1937 Germany ................................ 2/13

Primary Examiner—Peter Nerbun
Attorney, Agent, or Firm—Shefte, Pinckney & Sawyer

[57] ABSTRACT

An eye shielding method and apparatus is provided for eyeglass wearers including a generally planar shield having a plurality of notches and score lines formed therein to allow the generally planar shield to be bent into a configuration which substantially covers the peripheral region of the user's head not covered by standard eyeglasses. Mounting slots are provided to mount the shield on the temple of a conventional pair of eyeglasses. The shields may be manufactured in pairs and joined by a frangible joint.

12 Claims, 2 Drawing Sheets

EYE SHIELDING APPARATUS AND METHOD

BACKGROUND OF THE INVENTION

The present invention relates generally to eye protection devices and, more particularly, to an eye shielding apparatus and method for attachment to a pair of eyeglasses providing shielding in a region peripheral to the wearer's head.

In most industrial environments, safety glasses are required for eye protection. Safety glasses are typically constructed and configured as goggles which fit tightly to the user's face or in a manner similar to conventional eyeglasses. With regard to the latter, a frame is provided which rests on the user's face and includes two lens-bearing apertures fitted with non-correcting, substantially shatterproof lenses. Two support members, known as temples, extend rearwardly from the lens-bearing frame portion to rest on a wearer's ears for supporting the eyeglasses on a user's head. To protect the aforesaid peripheral region, side shields are typically permanently mounted to the frame. Generally, most industrial plant workers will have their own safety glasses, while additional safety glasses are maintained "on-site" for use by visitors.

Problems arise, however, when a person wearing vision correcting eyeglasses must use safety glasses. Although the aforesaid goggle-types will typically fit over a pair of eyeglasses, vision may be distorted or the goggle types may be unavailable. Often, a person will have to rely on their own eyeglasses for protection, and while conventional eyeglasses may provide protection in front of the eyes with the lenses, most conventional eyeglasses do not have shields formed on, or mounted to, the sides thereof, so that a region peripheral to the wearer's head and rearwardly of the lens-bearing frame of the eyeglasses is left exposed and unprotected. Accordingly, there exists a need for a supplemental side shield which can be attached to most conventional eyeglass frames to provide protection in the peripheral region.

Lindblom U.S. Pat. No. 2,932,066 teaches a supplemental eye shield molded to curve around a specific singular lens shape which is attached to the temples of a conventional pair of eyeglasses using rivets.

Liautaud et al U.S. Pat. No. 3,436,761 teaches side shields which are attachable to a conventional pair of eyeglasses, and which are easily mounted thereto. However, the shields of Liautaud et al require a specially designed instrument to remove the shields and do not provide complete coverage in the area near the lenses.

Bennett U.S. Pat. No. 3,505,679 teaches detachable side shields for eyeglasses which have a mounting arrangement molded therein. The Bennett shields are configured for use with a singular eyeglass frame configuration with respect to temple size and lens curvature.

Hinrichs U.S. Pat. No. 4,726,075 teaches disposable side shields for eyeglasses which are held to the frames using adhesive.

Known side shields are not configured for ease of manufacture and packaging and are not readily adaptable to a wide variety of eyeglasses without substantial structural modifications.

SUMMARY OF THE INVENTION

It is accordingly an object of the present invention to provide an eye shielding apparatus and method which addresses the above-discussed problems. Specifically, it is an object of the present invention to provide an eye shielding apparatus and method which provides an easily manufacturable and packagable eye shield which is disposable and is mountable on the temples of most conventional eyeglasses. It is further an object of the present invention to provide an eyeglass shield which is bendable to substantially enclose the region peripheral to the wearer's head regardless of the size and shape of the lens, or temple, or both.

The eye shielding apparatus of the present invention provides a safety shield for removable attachment to eyeglasses of the type having a frame with two lens-bearing apertures and two rearwardly extending temples, and includes a generally planar panel having a main body portion, a first end portion and at least one side portion extending along the length of the main body portion. An adjustment arrangement is provided for bending the panel into a shielding configuration, including a first scoring line formed between the main body portion and the side portion, the side portion to be folded about the first scoring line and away from the plane of the main body portion. A mounting arrangement is provided for mounting the shield on the temple of the eyeglasses in a manner that substantially covers a non-planar region peripheral to the eyeglass wearer's head and located rearwardly of the lens-bearing frame. The "peripheral region" to the head of the user is herein defined to be that region adjacent the frame of the eyeglasses on the user's head, immediately above and below the temples of the eyeglasses, and rearwardly of the lenses.

Preferably, the adjustment arrangement includes a score line arrangement formed in the first end portion for folding the end portion away from the plane of the main body portion to more fully enclose the peripheral region in the area adjacent the apertures of the frame. The shield preferably includes two notches formed in the first end portion to define three outwardly projecting segments of the first end portion, and a second score line arrangement includes three separate score lines disposed adjacent the outwardly projecting segments for folding each said segment individually away from the plane of the main body portion. It is further preferred that the shielding apparatus include a second side portion, and that the adjustment arrangement further include a second scoring line formed between the main body portion and the second side portion for folding the second side portion away from the plane of the main body portion to more fully enclose the peripheral region.

It is also preferred that the mounting arrangement include a plurality of slots formed in the main body portion extending longitudinally between the side portions for inserting a temple therethrough to removably mount the shield on the eyeglasses.

The shields are preferably integrally formed in pairs, and are joined at one end thereof with a frangible joint therebetween. The shields include a second end portion and the pairs of shields include two mirror image shields joined at the second end portions thereof, forming a right side shield and a left side shield and are preferably formed of a substantially transparent thermoplastic material.

According to the preferred method of the present invention, the eyes of an eyeglass wearer are shielded by providing a shield as above described, attaching the shield member to a pair of eyeglasses by passing the temples of the eyeglasses through a selected one of the slots formed in the shield with the first end portion of the shield adjacent the lens-bearing frame, bending a side portion along one of the score lines away from the plane of the main body portion into a shielding disposition with the head of the wearer and bending at least one of the outwardly projecting end portion segments inwardly toward a user's head and away from the plane of the main body portion for substantially covering the peripheral region. The method of the present invention may also include the step of bending the second side portion at the second scoring line away from the plane of the main body portion and toward the wearer's head for enhancing the coverage by the shield of the non-planar peripheral region.

DETAILED DESCRIPTION OF THE PREFERRED EMBODIMENT

Figure 1:
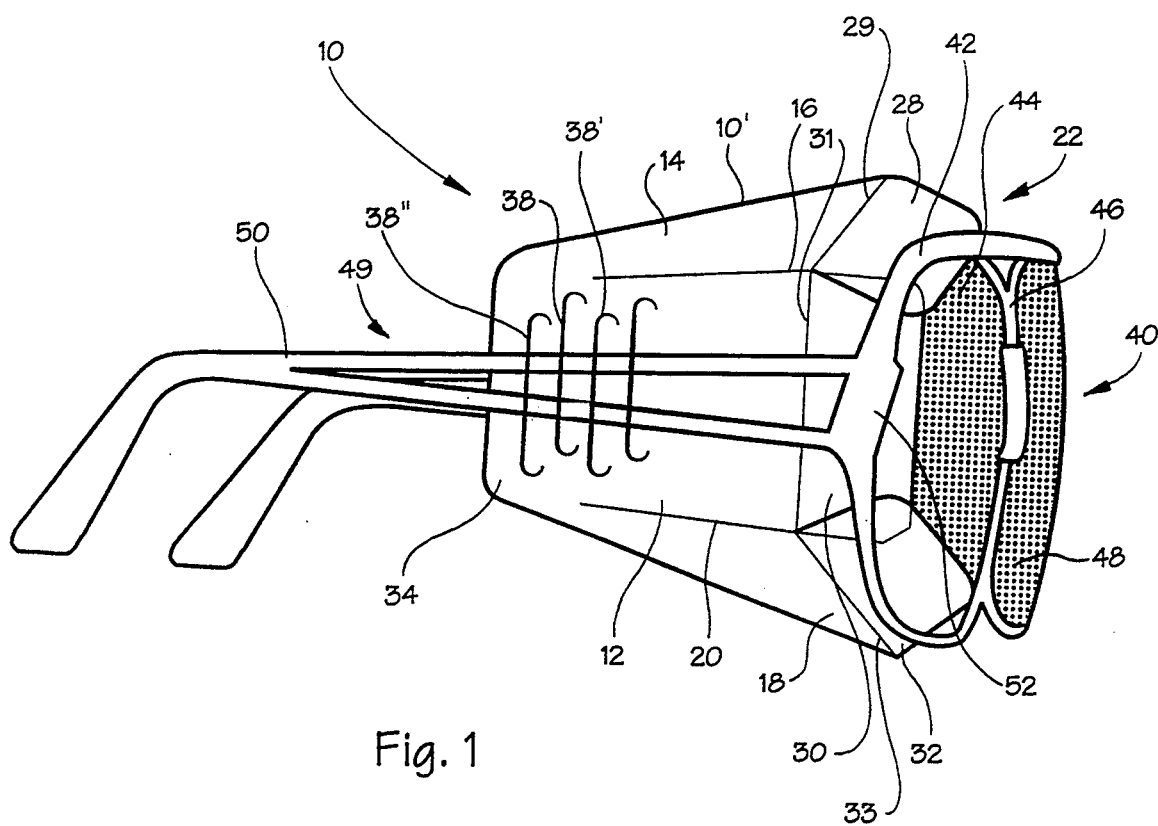
FIG. 1 is a side view of an eye shielding apparatus according to the preferred embodiment of the present invention shown attached to a pair of eyeglasses.

Referring now to the accompanying drawings, and particularly to FIG. 1, an eye shielding apparatus is shown generally at 10 mounted to a pair of conventional eyeglasses 40. The eyeglasses 40 include a frame 42 having two lens-bearing portions 44, each defining a lens-receiving opening, disposed in a side-by-side relationship, joined by a bridge 46, and two lenses 48 mounted to the frame 42 for sight therethrough, each lens 48 being shaped to conform to and fit snugly within the lens-receiving openings within the frame portions 44. The lenses 48 are separated by the bridge 46 which allows the frame 42 to traverse the face of the wearer while resting the frame 42 on the bridge of the wearer's nose. A supporting assembly 49 includes two elongate members 50, commonly known as temples, pivotably mounted respectively to the outward opposite sides of the frame portions 44 at a position closely adjacent the lenses 48, using hinges 52. The supporting assembly 49 assists the bridge 26 in positioning and stabilizing the eyeglass assembly 40 on the head of a wearer.

Figure 2:
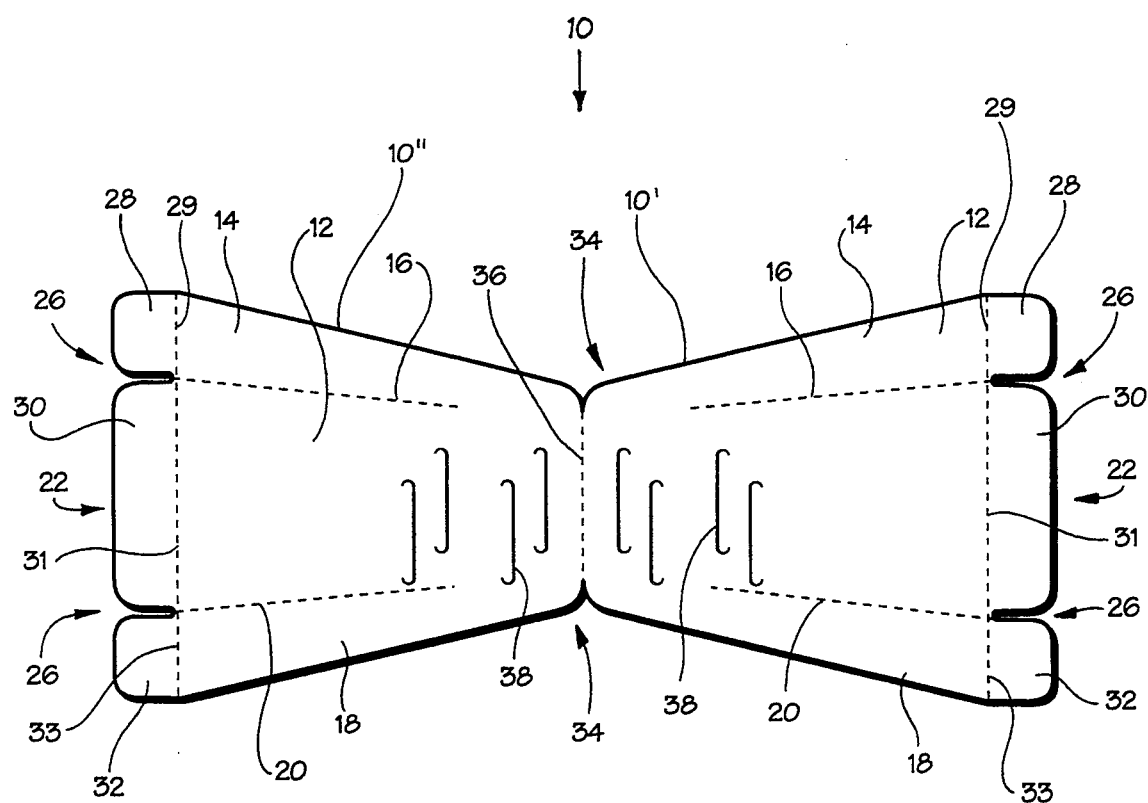
FIG. 2 is a side view of a pair of eye shields illustrated in FIG. 1 shown as a joined pair prior to attachment to a pair of eyeglasses.

Referring now to FIG. 2, the eye shielding apparatus 10 of the present invention is preferably includes a pair of shield 10',10" which are the mirror image of one another and which are formed integrally as a pair, thus providing one right side shield 10' and one left side shield 10", which are interchangeable as will be explained in greater detail hereinafter. Each single shield 10',10" is formed as a generally planar trapezoidal panel having a relatively wide first end portion 22 and a relatively narrow second end portion 34. A main body portion 12 extends between the end portions 22,34, and side portions 14,18 extend between the end portions 22,34, and along the main body portion 12.

In order for each shield 10',10" to provide substantial coverage of the peripheral region previously discussed, it must be bent from its planar configuration into a more curved configuration. Specifically, the regions around the lens and above and below the temples are not adequately covered with a flat shield, and some sort of curvature must be imparted to the shield to achieve the necessary covering configuration. Accordingly, the side portions 14,18 are bendable to cover the area above and below the temple, while the first end portion 22 is bendable inwardly to conform generally to the region around the lens. The present invention offers several features which enhance the ability of the shield to be configured to substantially cover the peripheral region.

One problem which arises when the side portions 14,18 are bent inwardly with respect to the main body portion, and the first end portion 22 is likewise required to be bent inwardly with respect to the main body portion 12. Since the first end portion 22 is generally orthogonal to the side portions 14,18, simultaneous inward bending of the first end portion 22 and the side portions 14,18 becomes difficult. In order to overcome this, and with continued reference to FIG. 2, two notches 26 are formed in the first end portion 22 adjacent the side portions 14,18 and extend inwardly a short distance toward the main body portion 12. The notches 26, and score lines 29,31,33 define two corner segments 28,32 and a middle segment 30 of the first end portion 22. The corner segments 28,32 are smaller than the middle segment 30 due to the positioning of the notches 26. The notches 26 allow the two outward segments 28,32 to bend individually and separately from the middle segment 30 as will be explained in greater detail hereinafter.

In order to enhance the ability of each shield 10',10" to bend, and to most effectively bend each shield 10',10" for maximum coverage, a plurality of score lines, formed as shallow indentations in the shield surface, are provided. A first side score line 16 extends intermediate the main body portion 12 and the first side portion 14, and from the notch 26 intermediate a first corner segment 28 and the middle segment 30 of the first end portion 22, rearwardly toward the second end portion 34. A second side score line 20 extends intermediate the main body portion 12 and the second side portion 18 from the other notch 26, rearwardly toward the second end portion 34.

To enhance the ability of the first end portion 22 to bend, the score lines 29,31,33 are formed in the first end portion 22 at the rearward extent of the notches 26, and they extend generally orthogonally to the side score lines 16,20. The first end score line 29 extends from one side edge of the shield 10',10" inwardly to the rearward extent of the notch 26 intermediate the first corner segment 28 and the first side portion 14. The second end score line 31 extends between the notches 26 at their rearward extent intermediate the main body portion 12 and the middle end segment 30. The third score line 33 extends from the other side edge of the shield 10 inwardly to the rearward extent of the other notch 26 intermediate the second corner segment 32 and the second side portion 18. Accordingly, the corner segments 28,32 are bendable independently of the middle end segment 30. The combination of scoring lines and notches allows the generally flat shield 10',10" to be configured to cover the non-planar peripheral region.

In order to mount each shield 10',10" onto the temples 50 of a pair of eyeglasses 40, as seen in FIG. 1, a plurality of slots 38 are formed in each shield 10',10" adjacent the second end portion 34. The slots 38 extend intermediate the side portions and, when the shield is worn by a user, the slots extend vertically. It is preferred that four slots 38 be arranged in series from the second end portion 34 inwardly toward the main body portion 12. Every alternate slot 38 is closer to one side portion 14,18 of the shield than the preceding slot 38 so as to provide a staggered arrangement of two pairs of slots and allow the user to mount the shield 10 onto a pair of eyeglasses in the most effective coverage orientation to fit the individual requirements of the user and the associated eyeglasses, as will be explained in greater detail presently.

For ease of manufacture, the shielding apparatus 10 of the present invention is die-cut from a transparent thermoplastic material in integral, mirror image pairs. With reference to FIG. 2, the left side shield 10" of a pair is attached to the right side shield 10' at the relatively narrow end portions 34 using a frangible joint 36. Accordingly, the eye shielding apparatus 10 can be packaged in a relatively flat configuration with the two required shields 10',10" in a single package, thereby assuring that the user will have the requisite two shields in a package conveniently adaptable for use in an industrial environment.

In operation, and according to the method of the present invention, eye shielding is accomplished by separating the left side shield 10" and the right side shield 10' at the frangible joint 36. Adjustability is enhanced by bending the side portions 14,18 inwardly away from the main body portion 12 of the shield at the score lines 16,20 and bending the individual end segments 28,30,32 inwardly away from the main body portion 12 of the shield at their respective score lines 29,31,33 prior to mounting the shields 10',10" onto a pair of eyeglasses 40. Referring now to FIG. 1, the right side shield 10' is mounted to the temple 50 of a pair of eyeglasses 40 by first orienting the shield with the wider first end portion 22 directed towards the lens area of the eyeglasses 40. Due to the staggered nature of the slots 38, the shield 10' can be positioned to provide substantial coverage of the peripheral region regardless of the relative position of the temple 50 on a particular user's head. To mount the shield 10' on the temple 50, the temple 50 is passed through a first slot 38' and then back through a second slot 38" of a staggered pair. This results in a portion of the shield 10' being positioned inwardly of the temple 50 and a portion of the shield being positioned outwardly of the temple 50.

The side portions 14,18 are then bent at the side score lines 16,20 to substantially cover the peripheral region above and below the temples 50 of the user, and the end segments 28,30,32 are bent inwardly at their respective score lines 29,31,33 to more fully cover the peripheral area in the region of the lens 48 of the eyeglasses 40. As can be seen in FIG. 1, the inclusion of notches 26 allows the middle end segment 30 to overlap the two corner segments 28,32 while the side portions 14,18 remain undisturbed by the bending of three the end segments 28,30,32. The same steps are then repeated for the left side shield 10". In this manner, a planar shield 10',10" may be bent into a covering relation with the decidedly non-planar peripheral region.

By virtue of the above, the present invention provides a supplemental eye shielding apparatus and method which may be inexpensively manufactured and packaged in a space-saving flat configuration, and which may be mounted to the temples of virtually any eyeglasses to provide inexpensive and easy-to-use supplemental eye shielding when safety glasses are required by eyeglass wearers.

It will therefore be readily understood by those persons skilled in the art that the present invention is susceptible of a broad utility and application. Many embodiments and adaptations of the present invention other than those herein described, as well as many variations, modifications and equivalent arrangements will be apparent from or reasonably suggested by the present invention and the foregoing description thereof, without departing from the substance or scope of the present invention. Accordingly, while the present invention has been described herein in detail in relation to its preferred embodiment, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements, the present invention being limited only by the claims appended hereto and the equivalents thereof.

I claim:

1. An eye shielding apparatus for removable attachment to eyeglasses of the type having a frame with two lens-bearing apertures and two rearwardly extending temples, said shield comprising:
   a generally planar panel having a main body portion, a first end portion and at least one side portion extending along the length of said main body portion;
   adjusting means for bending said panel into a shielding configuration, including a first scoring line formed between said main body portion and said side portion to permit said side portion to be folded about said first scoring line and away from the plane of said main body portion, scoring line means formed in said first end portion for folding said first end portion away from said plane of said main body portion and two notches formed in said first end portion to form three outwardly projecting segments, said scoring line means including three score lines disposed adjacent said outwardly projecting segments for folding each said segment individually away from the plane of said main body portion to enhance coverage of said shield for a variety of different eyeglass configurations; and
   means for mounting said shield on the temple of the eyeglasses, whereby said shield is mounted on the temple for substantially covering a non-planar region adjacent the eyeglass wearer's eyes peripheral to the eyeglass wearer's head and rearwardly of the lens-bearing frame, especially in an industrial environment.

2. An eye shielding apparatus according to claim 1 wherein said shield further includes a second side portion and said adjusting means further includes a second scoring line formed between said main body portion and said second side portion for folding said second side portion away from the plane of said main body portion to more fully enclose the peripheral region.

3. An eye shielding apparatus according to claim 1 wherein said mounting means includes a plurality of slots formed in said main body portion extending longitudinally between said side portions for inserting a temple therethrough to removably mount said shield on the eyeglasses.

4. An eye shielding apparatus according to claim 1 wherein said shields are integrally formed in pairs, said shields being joined at one end thereof with a frangible junction therebetween.

5. An eye shielding apparatus according to claim 4 wherein said panel includes a second end portion and said pairs include two mirror image shields joined at the second end portions thereof, forming a right side shield and a left side shield.

6. An eye shielding apparatus according to claim 1 wherein said shield is formed of a thermoplastic material.

7. An eye shielding apparatus for removable attachment to eyeglasses of the type having two lens-bearing apertures and two rearwardly extending temples, said shield comprising:

a generally planar panel having a main body portion, a first end portion and at least two side portions extending along the length of said main body portion;

adjusting means for bending said panel into a shielding configuration including two notches formed in said first end portion to define three outwardly projecting segments thereof, and two scoring lines formed between said main body portion and said side portions and generally aligned with said notches to permit said side portions to be folded about said scoring lines and away from the plane of said main body portion; and a score line arrangement including three score lines disposed adjacent said outwardly projecting segments for folding each said segment individually away from the plane of said main body portion for enhanced shielding; and means for mounting said shield on the temple of the eyeglasses including a plurality of slots formed in said main body portion wherein said slots are formed in pairs with a first pair of slots disposed at a first predetermined location and a second pair of slots disposed at a second predetermined location displaced a predetermined distance below and away from said first pair of slots to allow said shields to be used with a variety of eyeglasses for inserting a temple through a selected pair of slots to removably mount said shield on the eyeglasses for substantially covering a non-planar region adjacent the eyeglass wearer's eyes, peripheral to the eyeglass wearer's head and rearwardly of the lens-bearing frame, especially in an industrial environment.

8. An eye shielding apparatus according to claim 7 wherein said shields are integrally formed in pairs, said shields being joined at one end thereof with a frangible junction therebetween.

9. An eye shielding apparatus according to claim 7 wherein said panel includes a second end portion and said pairs include two mirror image shields joined at the second end portions thereof, forming a right side shield and a left side shield.

10. An eye shielding apparatus according to claim 7 wherein said shield is formed of a thermoplastic material.

11. A method for shielding the eyes of an eyeglass wearer, especially in an industrial environment, the eyeglasses being of the general type having a frame with two lens-bearing apertures and two rearwardly extending temples, said method comprising the steps of:

providing a shield member formed from a generally planar panel having a main body portion, a first end portion and at least one side portion extending along the length of said main body portion, and adjusting means including two notches formed in said first end portion defining three outwardly projecting and portion segments; a plurality of score lines including a score line extending between said main body portion and said side portion and three score lines extending along said end portion intermediate said notches; and mounting means including a plurality of slots formed in pairs with a first pair being disposed at a first predetermined location and a second pair being disposed at a second predetermined location in said main body portion;

attaching said shield member to a pair of eyeglasses by passing the temple of the eyeglasses through a selected pair of said slots, with said first end portion adjacent the lens-bearing frame;

bending a side portion along one of said score lines away from the plane of said main body portion into a shielding disposition with the head of a wearer; and bending at least one of said outwardly projecting end portion segments inwardly toward a user's head and away from the plane of the main body portion for substantially covering the non-planar region peripheral to the eyeglass wearer's head and rearwardly of the lens-bearing frame.

12. A method for shielding the eyes of an eyeglass wearer according to claim 11 wherein said shield member includes a second side portion extending along the length of said main body portion and a score line intermediate said second side portion and said main body portion, and said method further comprises the step of bending said second side portion at said scoring line away from the plane of said main body portion and toward the wearer's head for enhancing the coverage by said shield of the non-planar region peripheral to the wearer's head and rearwardly of the lens-bearing frame.

* * * * *

UNITED STATES PATENT AND TRADEMARK OFFICE
CERTIFICATE OF CORRECTION

PATENT NO. : 5,388,269

DATED : February 14, 1995

INVENTOR(S) : Bradley P. Griffin

It is certified that error appears in the above-identified patent and that said Letters Patent is hereby corrected as shown below:

Column 3, line 49, delete "is".

Column 3, line 50, delete "shield" and insert therefor -- shields --.

Column 4, line 9, delete ", and" and insert therefor -- is that --.

Column 5, line 52, delete "three the" and insert therefor -- the three --.

Column 8, line 17, delete "and" and insert therefor -- end --.

Signed and Sealed this

Twenty-sixth Day of December, 1995

Attest:

BRUCE LEHMAN

*Attesting Officer*   *Commissioner of Patents and Trademarks*